United States Patent [19]

Williams et al.

[11] Patent Number: 4,478,935
[45] Date of Patent: Oct. 23, 1984

[54] MANGANESE-CONTAINING ANTIBIOTIC AGENTS

[75] Inventors: Robert D. Williams; David R. Bright; Vernon V. Young; Jerome L. Martin, all of Terre Haute, Ind.

[73] Assignee: International Minerals & Chemical Corp., Terre Haute, Ind.

[21] Appl. No.: 422,408

[22] Filed: Sep. 20, 1982

Related U.S. Application Data

[62] Division of Ser. No. 196,722, Oct. 8, 1980, abandoned.

[51] Int. Cl.$^3$ ............... C12P 19/60; C12P 19/56; C12P 17/18
[52] U.S. Cl. ............... 435/75; 435/118; 435/119; 435/121; 435/125; 435/78; 424/283
[58] Field of Search ............... 435/118, 119, 121, 125, 435/75, 78

[56] References Cited

U.S. PATENT DOCUMENTS

| | | | |
|---|---|---|---|
| 3,873,715 | 3/1975 | Pressman et al. | 424/283 |
| 3,907,832 | 9/1975 | Hamill | 424/283 X |
| 3,923,823 | 12/1975 | Gale et al. | 424/272 X |
| 3,985,893 | 10/1976 | Holland et al. | 424/272 |
| 4,058,620 | 11/1977 | Westley | 424/283 |
| 4,076,834 | 2/1978 | Westley | 424/283 |
| 4,083,968 | 4/1978 | Westley | 424/181 |
| 4,100,171 | 7/1978 | Westley et al. | 424/274 |
| 4,129,578 | 12/1978 | Celmer et al. | 424/283 X |
| 4,129,659 | 12/1978 | Pressman et al. | 424/283 |
| 4,148,890 | 4/1979 | Czok et al. | 424/181 |
| 4,161,520 | 7/1979 | Osborne et al. | 424/115 |
| 4,164,586 | 8/1979 | Westley | 424/283 |
| 4,181,573 | 1/1980 | Westley et al. | 435/119 |

OTHER PUBLICATIONS

Pfeiffer et al., Biochemistry, vol. 15, No. 5, pp. 935-943 (1976).
Pressman, Ann. Rev. Biochemistry 1976, pp. 501-530.
Liu et al., Journal of Antibiotics (Japan), vol. 32, pp. 95-99 (1979).
Westley et al., Journal of Antibiotics (Japan), vol. 32 pp. 100-107 (1979).
Westley, Advances in Applied Microbiology, vol. 22, pp. 177-223 (1977).

*Primary Examiner*—Lionel M. Shapiro
*Attorney, Agent, or Firm*—Bernard, Rothwell & Brown

[57] ABSTRACT

Manganese complexes of various monovalent and divalent polyether antibiotics are provided which act as coccidiostats and growth promoting agents when administered to food-producing animals such as cattle, sheep, swine and poultry. Soluble manganese salt is added to a fermentation beer containing the polyether antibiotics to form an insoluble, recoverable biomass containing the desired manganese antibiotic complex. This biomass, in a dried form, can be given orally to animals such as cattle, sheep, swine and poultry.

The subject manganese complexes include: linear monovalent and divalent polyethers (monensin, nigericin, lasalocid, lysocellin, etc.); non-glycolic monovalent monoglycoside polyethers (septamycin, dianemycin, lenoremycin, carriomycin and antibiotic A-204); mononitrogen-containing divalent pyrrole ethers (calcimycin, X-14547, etc.); polynitrogen-containing divalent pyrrole ethers (A-23187, etc.); glycolic monovalent monoglycoside polyethers (etheromycin, etc.); other polyether antibiotics including ionomycin, aabomycin, disnerycin, duamycin, BL-580, K-41, SF-1195, M-4164A, A-32887, 30,504RP, 38,986, 44,161, 47,433, 47,434 and 47,224. The above manganese complexes are also active agents for improving cardiovascular function in animals.

Purified manganese-containing antibiotic complexes can be extracted from the biomass using suitable organic solvents, followed by crystallization or precipitation of the purified complexes. The purified products can be administered as boluses, subcutaneous implants, or as injectable preparations.

19 Claims, No Drawings

MANGANESE-CONTAINING ANTIBIOTIC AGENTS

This is a division of copending application Ser. No. 196,722, filed Oct. 8, 1980, now abandoned.

BACKGROUND

This invention relates to manganese complexes of various polyether antibiotics as new compositions of matter, processes for making these manganese complexes, and to processes for the administration of manganese complexes of polyether antibiotics to food-producing animals such as cattle, sheep, swine, and poultry to promote growth, to enhance feeding efficiency, and/or to combat coccidial infections. The subject manganese complexes of polyether antibiotics may be administered orally as feed additives in the crude form, or may be first purified, and administered as boluses, parenterally as injections, or as subcutaneous implants.

Cardiovascular function in animals may be improved by administering manganese complexes of polyether antibiotics. The manganese complexes of polyether antibiotics formed in fermentation beers as described herein may be purified further for pharmaceutical use in humans.

Polyether antibiotics can be generally characterized as carboxylic acid ionophores which can be produced by growing Streptomyces type microorganisms in suitable nutrient media. These polyether antibiotics have a basic structure generally consisting essentially of the elements oxygen, hydrogen and carbon (and sometimes nitrogen) and have a molecular weight in the range of about 300 to about 1800, most often from about 400 to about 1200. They have low solubility in water, are generally soluble in low molecular weight alcohols, ethers, and ketones; and have at least one, and usually one or two, carboxylic acid groups. A generally comprehensive review of this class of antibiotics is set forth in Westley, *Adv. Appl. Microbiology* 22, 177-233 (1977). As is mentioned therein, at least twenty different polyether antibiotics were known at the time the article was written. Since then, additional polyether antibiotics have been discovered.

In Westley (op. cit.), the known polyether antibiotics are divided into four separate classes based on the ability of the particular antibiotic to effect the transport of monovalent and divalent cations and based on the chemical structure of the particular antibiotic. Westley's classification system is adopted herein.

Westley defined Class 1a as monovalent polyether antibiotics. In addition, the Class 1a polyether antibiotics have a generally linear configuration, i.e., the carboxylic portion of the polyether molecule is attached either directly or indirectly to a terminal ring structure, and include about four to six tetrahydropyran and/or -furan structures, and up to six total ring structures. Class 1a includes monensin, laidlomycin, nigericin, grisorixin, salinomycin, narasin, lonomycin, X-206, SY-1, noboritomycins A and B, mutalomycin and alborixin. Class 1a antibiotics may also be described as "linear monovalent polyether antibiotics".

According to Westley's system, monovalent monoglycoside polyether antibiotics belong to Class 1b. These polyether antibiotics include a glycoside type structure, more specifically, a 2,3,6-trideoxy-4-O-methyl-D-erythrohexapyranose moiety, which is attached to the polyether molecule such that a non-linear type molecule is formed, i.e., the carboxylic portion of the polyether molecule is attached either directly or indirectly to a non-terminal ring structure or the molecule has a side chain ring structure, e.g., a 2,3,6-trideoxy-4-O-methyl-D-erythrohexapyranose moiety. The polyether antibiotics of this class usually contain about six or seven tetrahydropyran and/or -furan structures.

Class 2a antibiotics as defined by Westley are divalent polyethers, and have a generally linear configuration. They may contain from about two to about three tetrahydropyran and/or -furan structures, and up to about three total ring structures. Nitrogen atoms are not present in the Class 2a molecules. Included within Class 2a are lasalocid and lysocellin. The Class 2a polyether antibiotics are hereinafter sometimes designated "non-nitrogen containing divalent polyether antibiotics".

Class 2b in Westley's system are divalent pyrrole polyethers. In contrast to the other classes, the Class 2b antibiotics contain one or more nitrogen atoms.

Lasalocid is included in Class 2a as defined by Westley. Lasalocid was discovered by Julius Berger et al in media fermented with a Streptomyces microorganism isolated from a sample of soil collected at Hyde Park, Mass. [Cf. Berger et al, *J. Am. Chem. Soc.* 73, 5295-8 (1951)]. Originally this material was known by the code name X-537A. About 1969 lasalocid was found to possess coccidiostatic activity. Later this activity was established for monensin, nigericin, salinomycin, and narasin all of which belong to Class 1a.

The polyether antibiotics have usually been recovered and employed in the form of their sodium salts. For example, a process for recovering lasalocid from its fermentation broth is disclosed in the Berger at al article (op. cit.). In this process, the antibiotic or its alkali metal salts are extracted into various organic solvents with subsequent evaporation of the solvents in a multi-step operation.

A process for the recovery of carriomycin from fermentation beer is described by Imada et al in *J. Antibiotics* 31, 7-14 (1978). In the disclosed process, fermented beer containing the cerriomycin antibiotic was adjusted in pH with concentrated NaOH and acetone was then added. After stirring the mixture for 1 hour at room temperature, mycelia were filtered off and extracted again with acetone. The extracts were combined and concentrated in a vaccum until no acetone remained. The concentrated aqueous solution was extracted twice with equal volumes of ethyl acetate, followed by drying with anhydrous $Na_2SO_4$. The extracts were concentrated in a vacuum and passed through a column of activated charcoal, then the column was washed with ethyl acetate. The fractions active against *Staphylococcus aureus* FDA 209P were combined and the solvent was evaporated. To the oily residue was added n-hexane. The resultant solid material was collected by filtration and crystallized from aqueous acetone. On recrystallization from aqueous acetone, crystals of the mixed sodium and potassium salts of carriomycin were obtained, the mixture was dissolved in aqueous acetone, and the solution was extracted twice with equal volumes of ethyl acetate. The extracts were dried with anhydrous $Na_2SO_4$ and concentrated to dryness in a vacuum. The resultant crystalline powder was recrystallized from aqueous acetone to yield carriomycin free acid.

As is apparent from the above example, such processes can be quite complicated and can require the use of relatively large quantities of various organic solvents, at least some of which may be quite expensive. In addition, such solvent recovery processes inevitably will suffer antibiotic yield losses as well as losses of the various organic solvents used in the process. There is thus a continuing need for antibiotic preparation and recovery processes which effectively and efficiently produce polyether antibiotics in a form suitable for use as feed additives.

GENERAL DESCRIPTION

Manganese complexes of polyether antibiotics can be advantageously formed by adding water-soluble manganese salts to the fermentation broth in which such antibiotics have been produced. When formed in a fermentation beer, the formation of these complexes facilitates the recovery of the polyether antibiotics from the fermentation beer in which the antibiotics have been produced by, among other things, avoiding the necessity of using recovery methods which involve extractions with organic solvents followed by their subsequent purification and reuse. The resulting broth-insoluble manganese complexes of the antibiotics can then be recovered from the broth and employed, for instance, as coccidiostatic, feeding efficiency improving and growth-promoting agents for poultry. Upon further purification, the recovered manganese complexes of these polyether manganese complexes may be utilized in stimulating cardiovascular function in animals.

An antibiotic-containing fermentation broth can be prepared in conventional manner by fermenting a nutrient-containing liquid fermentation medium inoculated with a Streptomyces microorganism capable of producing the desired antibiotic. Suitable liquid fermentation media are generally aqueous dispersions containing a source of assimilable nitrogen and carbohydrates. Nitrogen sources for use in the fermentation media herein can include, for example, yeast, yeast-derived products, corn meal, bean meal, e.g., soy bean meal, etc. Carbohydrate sources for use in the fermentation media herein can include, for example, sugar, molasses, corn-steep liquor and the like. The fermentation media can also contain a variety of optional ingredients, if desired, such as for example, pH adjustment agents, buffers, trace minerals, antifoam agents, filter aids, etc.

The antibiotic can be prepared by growing the Streptomyces microorganism in an aerated, agitated, submerged culture with the pH of the broth adjusted to about neutral, i.e., from about 6.5 to 7.5. Fermentation can generally be carried out as slightly elevated temperatures, e.g., between about 25° C. and 35° C. Incubation of the broth can be carried out for a period of several days, e.g., from about 4 to 6 days or longer if it is economically advantageous to do so.

The novel manganese complexes of the present invention can be formed from any of the known polyether antibiotics which include: linear monovalent and divalent polyethers (monensin, nigericin, lasalocid, lysocellin, etc.); non-glycolic monovalent monoglycoside polyethers (septamycin, dianemycin, lenoremycin, carriomycin and antibiotic A-204); mononitrogen-containing divalent pyrrole ethers (calcimycin, X-14547, etc.); polynitrogen-containing divalent pyrrole ethers (A-23187, etc.); glycolic monovalent monoglycoside polyethers (etheromycin, etc.); other polyether antibiotics including ionomycin, aabomycin, disnerycin, duamycin, BL-580, K-41, SF-1195, M-4164A, A-32887, 30,504RP, 38,986, 44,161, 47,433, 47,434 and 47,224.

Detailed descriptions of these antibiotics are presented in succeeding paragraphs.

DESCRIPTION OF SPECIFIC ANTIBIOTICS

A more detailed description of members of Westley's Class 1a polyether antibiotics is given below. These antibiotics have a generally linear configuration. Their manganese complexes can be made as described herein.

Monensin can be produced by inoculating the above described fermentation medium with a *Streptomyces cinnamonensis* microorganism. Such a microorganism is on unrestricted deposit under the number ATCC 15413 at the American Type Culture Collection, 12301 Parklawn Drive, Rockville, Md. 20852 (hereinafter referred to as the American Type Culture Collection).

Monensin is characterized chemically as 2-[5-ethyltet rahydro-5-[tetrahydro-3-methyl-5-[tetrahydro-6-hydroxy-6-(hydroxymethyl)-3,5-dimethyl-2H-pyran-2-yl]-2-furyl]-2-furyl]-9-hydroxy-β-methoxy-α,γ,2,8-tetramethyl-1,6-dioxaspiro[4.5]decane-7-butyric acid. This material has the following structural formula:

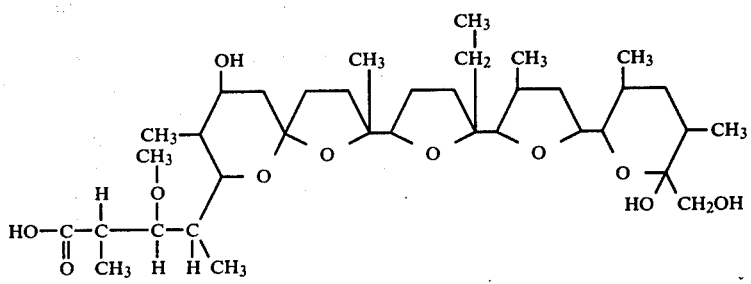

Monensin

Monensin is described in greater detail in U.S. Pat. No. 3,501,568 and U.S. Pat. No. 3,794,732.

Nigericin can be produced by inoculating the fermentation medium with a *Streptomyces violaceoniger* microorganism. Such a microorganism is on unrestricted deposit at NRRL B1356 at the Northern Research and Development Division, Agricultural Research Service, U.S. Department of Agriculture, Peoria, Ill. (hereinafter referred to as the Agricultural Research Service).

Nigericin is characterized chemically as a stereoisomer of tetrahydro-6-([9-methoxy-2,4,10-trimethyl-2-[-tetrahydro-5-methyl-5-[tetrahydro-3-methyl-5-[tetra hydro-6-hydroxy-6-(hydroxymethyl)-3,5-dimethyl-2H-pyran-2-yl]-2-furanyl]-2-furanyl]-1,6-dioxaspiro(4.5)-dec-7-yl]-methyl-α,3-dimethyl-2H-pyran-2-acetic acid). This antibiotic has the following structural formula:

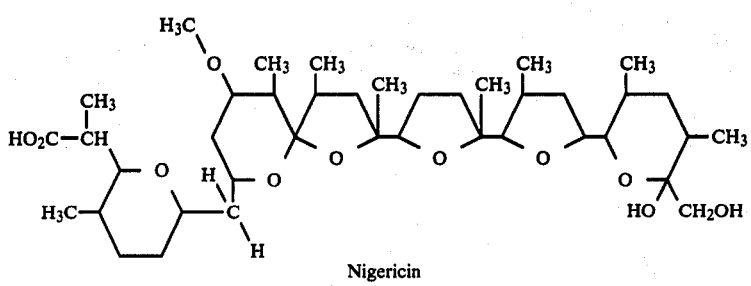

Nigericin

Nigericin is also known by the names polyetherin A, antibiotic X-464, antibiotic K178, helexin C and azolomycin M. Nigericin (and its characteristics and preparation) is described in greater detail in U.S. Pat. No. 3,555,150; U.S. Pat. No. 3,794,732, Harned et al, *Antibiotics and Chemotherapy*, Volume 1, Number 9 (December, 1951) pages 594–596; Steinrauf et al, *Biochemical and Biophysical Research Communications*, Volume 33, Number 1 (1968) pages 29–31 and Stempel et al, *The Journal of Antibiotics*, Volume XXII, Number 8 (August, 1969) pages 384–385.

Salinomycin can be produced by inoculating a fermentation medium with a *Streptomyces albus* microorganism which is on deposit under number ATCC 21838 at the American Type Culture Collection mentioned previously. Salinomycin was reported by Miyazaki et al, *J. Antibiotics* 27, 814–21 (1974) as having the following structural formula:

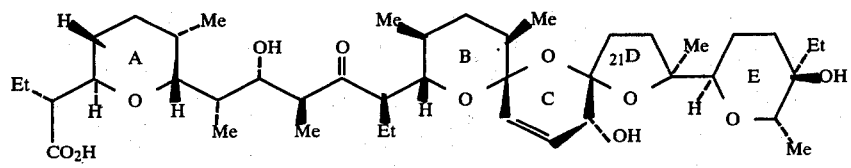

Salinomycin

The above article sets forth methods of preparation and properties of salinomycin and U.S. Pat. No. 3,857,948 to Tanaka et al also discloses methods for the preparation of the salinomycin antibiotic.

Narasin (also known as 4-methylsalinomycin) can be produced by inoculating a fermentation medium with a *Streptomyces aureofaciens* microorganism which is on unrestricted deposit at the Agricultural Research Service mentioned previously under culture numbers NRRL 5758 and 8092. The structure of narasin was reported by Berg et al, *J. Antibiotics* 31, 1–6 (1978) as the following:

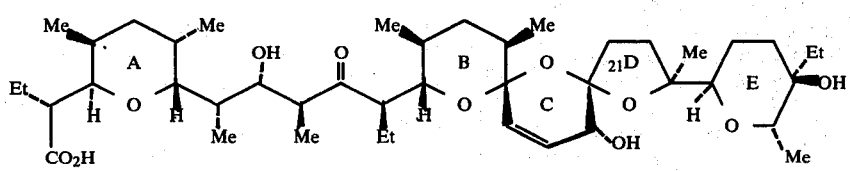

Narasin

The antibiotic is also the subject of U.S. Pat. Nos. 4,035,481 and 4,038,384 to Berg et al.

The antibiotics noboritomycin A and B are the fermentation products of the microorganism *Streptomyces noboritoensis* which is on deposit at Agricultural Research Service under the number NRRL 8123. A method for the preparation of these antibiotics and their chemical structure was reported by Keller-Juslén et al in *J. Antibiotics* 31, 820–828 (1978). The antibiotics have the structural formula:

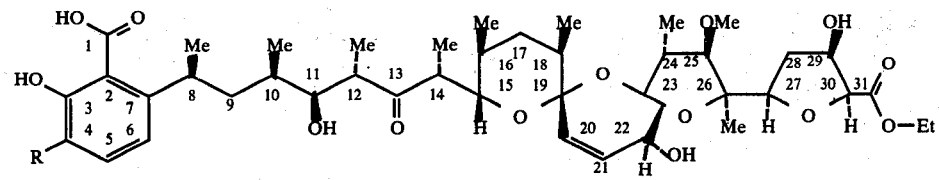

Noboritomycin A & B

In noboritomycin A, R is methyl and in noboritomycin B, R is ethyl.

The antibiotic grisorixin is produced from the microorganism *Streptomyces griseus* as reported by Gachon et al, *Chem. Comm.*, 1421–1423 (1970) and *J. Antibiotics* 28, 345–350 (1975). As is disclosed in U.S. Pat. No. 4,161,520 to Osborne et al, the microorganism is on deposit at the Institut National de la Recherche Agronomique where it has been assigned the designation INRA SAB 2142. Grisorixin is structurally very similar to nigericin, the only difference being the presence of an additional oxygen in nigericin. The structural formula for grisorixin is:

ported by Rhone Poulenc: Japan Patent, Kokai No. 50-129, 796 (Oct. 14, 1975). U.S. Pat. No. 3,950,514 to Sawada et al discloses the Ionomycin antibiotic as being produced by the *Streptomyces ribosidicus* microorganism which has been deposited under number ATCC 31051 at the American Type Culture Collection.

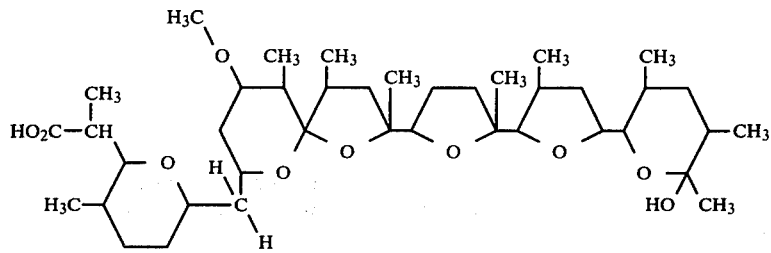

Grisorixin

Various derivatives of grisorixin are disclosed by Gachon et al, *J. Antibiotics* 28, 351–357 (1975).

Antibiotic X-206 was first reported by Berger et al, *J. Am. Chem. Soc.* 73, 5295–5298 (1951) and has the following structure as reported by Blount et al, *Chem. Comm.*, 927–928 (1971):

The following structural formula was determined by Gachon et al, *J. Antibiotics* 29, 603–610 (1976) for the antibiotic alborixin:

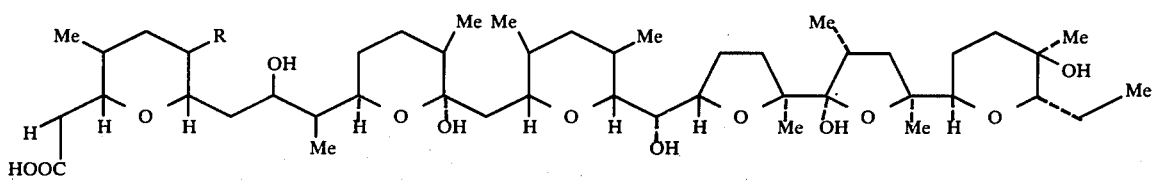

R = Me or H
Alborixin

Certain characteristics of the antibiotic were presented in the article by Delhomme et al, *J. Antibiotics* 29,

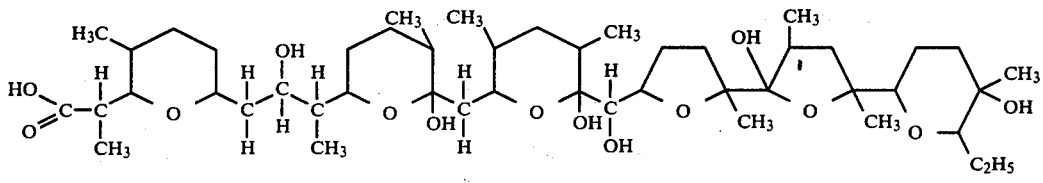

X-206

Methods for preparation of the X-206 antibiotic as well as further particulars as to its properties will be found in U.S. Pat. Nos. 3,839,557 to Raun and 3,794,732 to Raun.

The antibiotic Ionomycin has the following structural formula as reported by Mitani et al, *J. Antibiotics* 31, 750–755 (1978):

692–695 (1976). The alborixin antibiotic is produced from a *Streptomyces albus* microorganism and as is disclosed in U.S. Pat. No. 4,161,520 to Osborne et al, the microorganism is on deposit at the Institut National de la Recherche Agronomique and assigned the designation INRA SAB 3840.

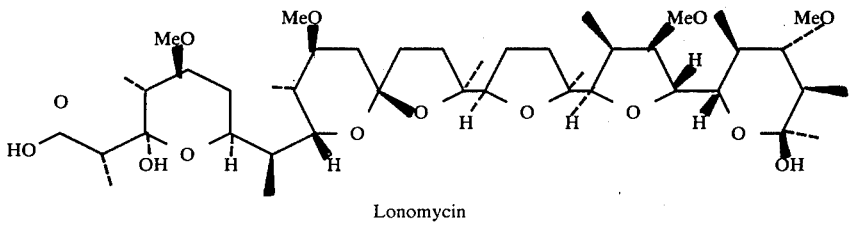

Lonomycin

A method for producing the antibiotic is given by Omura et al, *J. Antibiotics* 29, 15–20 (1976). The antibiotic was also identified by Oshima et al, *J. Antibiotics* 29, 354–365 (1976) as DE No. 3936 and was determined to be identical to emercid reported by Riche et al, *J.C.S. Chem. Comm.*, 951–952 (1975) and to 31,559RP re- Mutalomycin is produced by strain S11743/A of the *Streptomyces mutabilis* microorganism which has been deposited at the Agricultural Research Service under number NRRL 8088. A method for preparing the antibiotic and its physical and chemical properties were reported by Fehr et al, *J. Antibiotics* 30, 903–907 (1977). The structural formula of mutalomycin is:

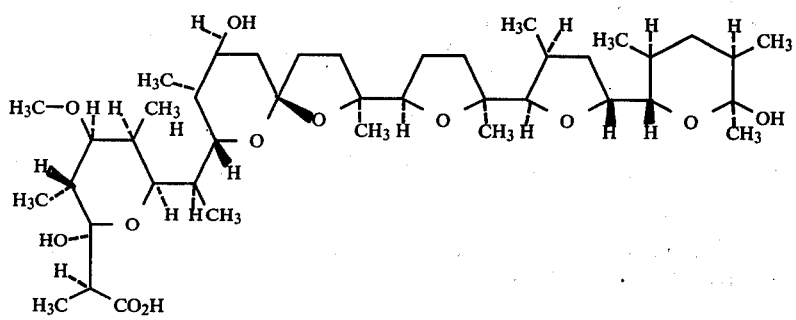

Mutalomycin as reported by Fehr et al, *J. Antibiotics* 32, 535–536 (1979).

The antibiotic laidlomycin has been described by Kitame et al, *J. Antibiotics* 27, 884–887 (1974), the antibiotic being produced by the *Streptomyces eurocidicus* var. *asterocidicus* microorganism which has been indexed as species S-822 at the Department of Bacteriology, Tohoku University School of Medicine, Sendai, Japan. The chemical structure of laidlomycin was reported by Westley, *Adv. Appl. Microbiology* 22, 177–223 (1977) as being:

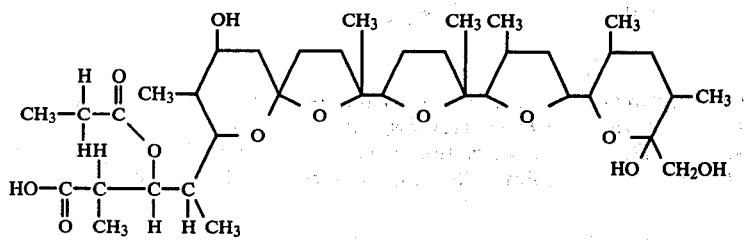

Laidlomycin

The laidlomycin antibiotic also appears to be the subject of U.S. Pat. No. 4,016,256 to Ishida et al.

The antibiotic SY-1 is the fermentation product of a *Streptomyces albus* microorganism, a culture of which has been deposited at the Americal Type Culture Collection under accession number ATCC 21838. As depicted in U.S. Pat. No. 4,138,496 to Shibata et al, antibiotic SY-1 has the following structural formula:

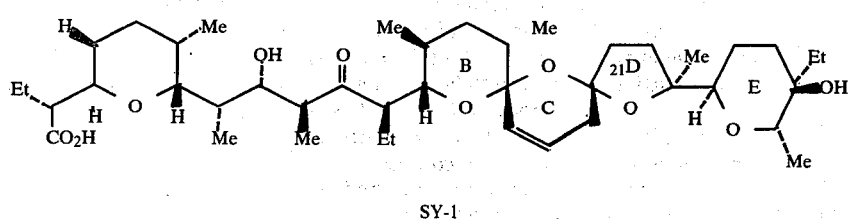

SY-1

The structure of antibiotic SY-1 is quite similar to that of salinomycin, the only apparent structural difference being that salinomycin contains a hydroxyl group on the ring designated "C".

Lasalocid can be prepared by inoculating the fermentation medium with a *Streptomyces lasaliensis* microorganism. Lyophilized tubes of this culture bearing the laboratory designation X-537A were originally deposited at the Agricultural Research Service under the identification number NRRL 3382. Replacement has been made with a culture given the identification number NRRL 3382R. A culture of this microorganism which produces lasalocid is also available from the American Type Culture Collection, Rockville, Md., under the number ATCC 31180.

The antibiotic lasalocid has been chemically identified in U.S. Pat. No. 4,164,586 to Westley as 6-(7(R)-[5(S)-ethyl-5(5(R)-ethyltetrahydro-5-hydroxy-6(S)-methyl-2H-pyran-2(R)-yl)tetrahydro-3(S)-methyl-2(S)-furyl]-4(S)-hydroxy-3(R),5-(S)-dimethyl-6-oxononyl)-2,3-cresotic acid. A manganese lasalocid complex, dissolved in methanol is described by Degani, et al, *Ion Binding by X-537A*, Biochem. 13, 5022–33 (1974). However, a solid manganese complex of lasalocid is not disclosed, and no utility for the manganese complex of lasalocid in methanol or hexane is disclosed. The stated purpose of the study was to determine formation constants.

The structural formula for lasalocid is as follows:

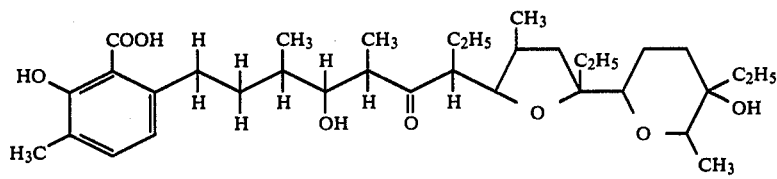

Lasalocid

A method for producing the antibiotic lysocellin was disclosed by Liu et al in U.S. Pat. No. 4,033,823. The method involves the cultivation of a strain of *Streptomyces longwoodensis* which is on deposit at the American Type Culture Collection under the designation ATCC 29251. The structure of lysocellin is as follows:

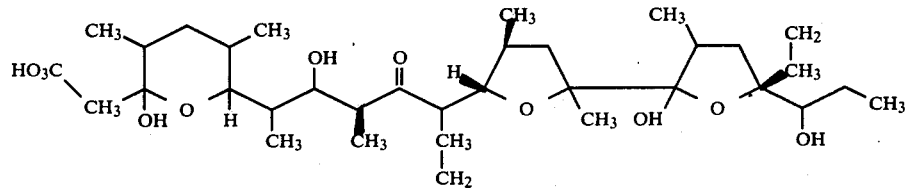

Lysocellin

Suitable method for preparing the lysocellin antibiotic are disclosed in the above-mentioned patent. The characteristics of lysocellin were first discussed in the article by Ebata et al, *J. Antibiotics* 28, 118–121 (1975).

Additional polyether antibiotics for forming the manganese complexes of the subject invention include the antibiotics septamycin, dianemycin, A-204, lenoremycin and carriomycin. These latter antibiotics are nonglycolic, monovalent monoglycoside polyethers in Westley's Class 1b.

Septamycin is also known as A-28695 and is the subject of U.S. Pat. Nos. 3,839,558 and 3,839,559 to Hamill et al. As is set forth by Keller-Juslén et al, *J. Antibiotics* 28, 854–859 (1975), the antibiotic has the structural formula:

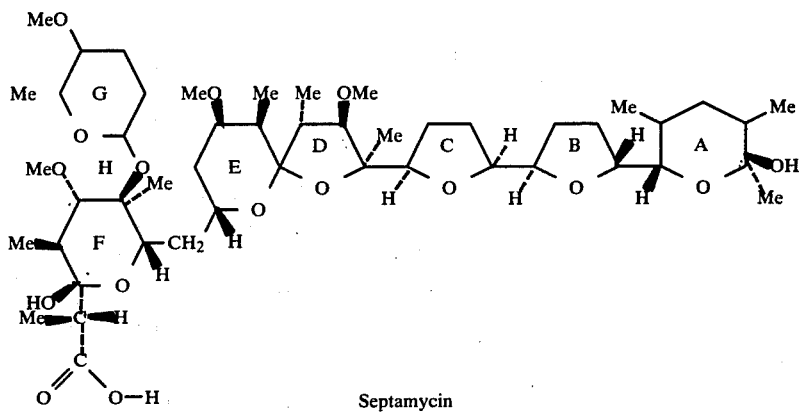

Septamycin

The antibiotic is produced from the cultivation of a *Streptomyces hygroscopicus* microorganism which has been deposited under number NRRL 5678 at the Agricultural Research Service. The abovementioned patents to Hamill et al classified the septamycin producing microorganism as a *Streptomyces albus* microorganism, a culture of which has been deposited at the Agricultural Research Service under accession number NRRL 3883. Further characteristics and a method for producing the antibiotic are set forth in the article by Keller-Juslén et al mentioned above.

Dianemycin is the fermentation product of a microorganism which is a strain of *Streptomyces hygroscopicus* which is on unrestricted deposit as NRRL 3444 at the Agricultural Research Service. Dianemycin was characterized by Steinrauf et al, *Biochemical and Biophysical Research Communications* 45, 1279–1283 (1971) as having the structure formula:

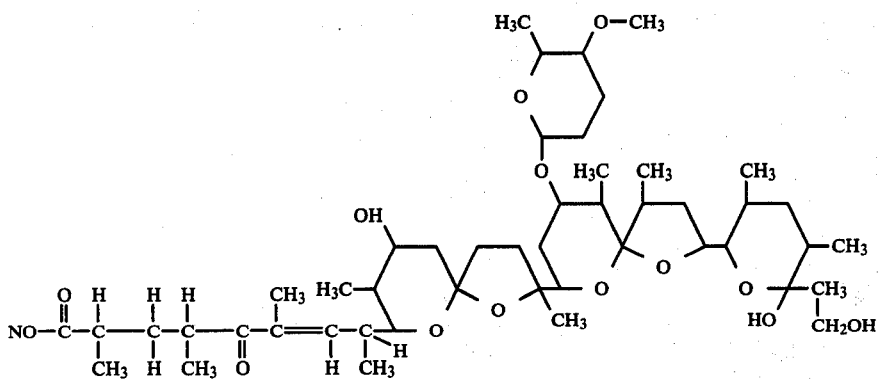

Dianemycin

U.S. Pat. No. 3,577,531 to Gorman et al and U.S. Pat. No. 3,711,605 to Hamill et al disclose the description, preparation and characteristics of dianemycin.

The antibiotic A-204 is described and a method for its preparation disclosed in U.S. Pat. No. 3,705,238 to Hamill et al and in U.S. Pat. No. 3,794,732 to Raun. The term A-204 is used to designate the different components obtained by fermentation in the presence of *Streptomyces albus* microorganism under aerobic conditions in a culture medium containing assimilable sources of carbon, nitrogen and inorganic salts. According to U.S. Pat. No. 3,794,732 to Raun, the organism capable of producing antibiotic A-204 has been placed on permanent deposit, without restriction, with the culture collection of the Agricultural Research Service, and is available to the public under culture number NRRL 3384.

Component I of A-204 is the most important and the most abundant. Component II constitutes about 5% of the mixture of A-204 components produced and the other components are obtained in smaller quantities. The structural formula shown below is that of the acid form of A-204 I.

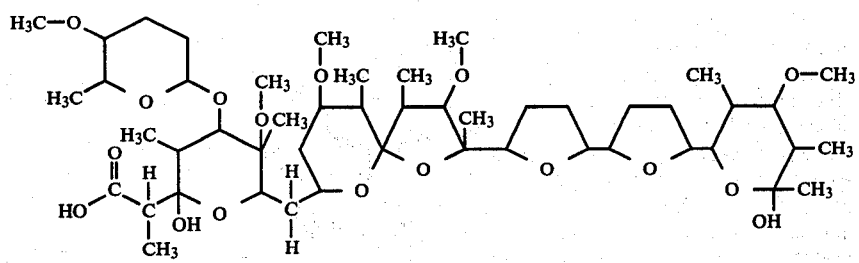

A-204 I

The antibiotic lenoremycin is the fermentation product of a *Streptomyces hygroscopicus* microorganism which is deposited under number ATCC 21840 at the American Type Culture Collection. The antibiotic was described by Kubota et al, *J. Antibiotics* 28, 931–934 (1975). The structure reported by Liu et al, *J. Antibiotics* 29, 21–28 (1976) is as follows:

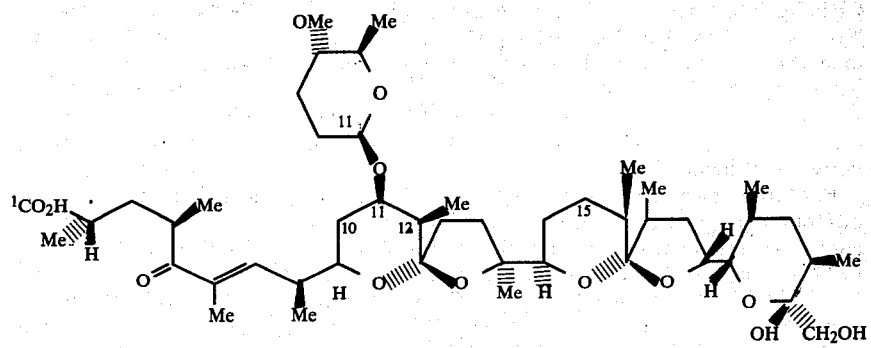

Lenoremycin

The Liu article also stated that lenoremycin is identical to the antibiotic A-130A described in Japanese patent publication No. 7304558 of Shionogi. The antibiotic A-130A is also the subject of U.S. Pat. No. 3,903,264 to Oikawa et al. The above structure is also reported in Blount et al, *Chem. Comm.* 853–855 (1975) who designated the antibiotic as Ro 21-6150.

The antibiotic carriomycin has the following structural formula as reported by Imada et al, *J. Antibiotics* 31, 7–14 (1978):

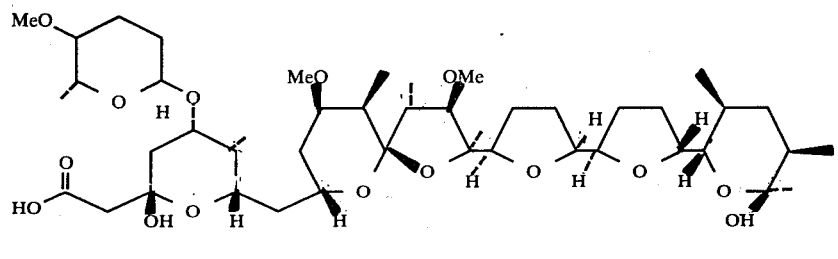

Carriomycin

The antibiotic is produced by strain T-42082 of the *Streptomyces hygroscopicus* microorganism which has been deposited at the Institute for Fermentation, Osaka, Japan, under accession number IFO 13609 and at the American Type Culture Collection under accession number ATCC 31080. The carriomycin antibiotic is the subject of U.S. Pat. No. 4,069,316 to Imada et al.

While the above description of the various known non-glycolic polyether antibiotics have generally identified the antibiotics as being single compounds, it should be recognized that at least some of these polyether antibiotics are produced as an antibiotic complex of structurally related factors containing varying proportions of each factor. As an example, the structure for A-204 set forth previously is A-204 factor I which is produced in combination with other factors in ratios depending upon fermentation conditions. It should, therefore, be realized that the present invention comprehends the manganese complexes of the various factors of the non-glycolic polyether antibiotics whether in combination with other factors or in their isolated form as well as their use in promoting growth, enhancing feeding efficiency and treating coccidial infections in poultry, and in stimulating cardiovascular function in animals. Furthermore, manganese complexes of derivatives of the previously mentioned non-glycolic polyether antibiotics are also within the scope of the present invention. For example, U.S. Pat. No. 3,985,872 to Chamberlin is directed to dihydro A-204 and U.S. Pat. No. 3,907,832 to Hamill is directed to monoether and monothioether derivatives of A-204. Therefore, as used herein, the specific name of the polyether antibiotic, e.g. A-204, encompasses all of the factors of the antibiotic, e.g. A-204 I and II, as well as isomers, homologs, and derivatives thereof.

For further particulars as to characteristics and methods for the preparation of certain of the above polyether antibiotics, reference is made to U.S. Pat. No. 3,995,027 to Gale et al and the patents cited therein and to U.S. Pat. No. 3,794,732 to Raun and the patents and articles cited therein.

The subclass 2b nitrogen-containing pyrrole ether antibiotics include the antibiotic X-14547 (mononitrogen, divalent) and the antibiotic A-23187 also known as calcimycin (polynitrogen-containing divalent). The pyrrole ether antibiotic known under the code designation X-14547 is characterized chemically as α-(R), 5(S)-dimethyl-6(R)-1-ethyl-4-[4-(R)-(2)pyrrolylcarbonyl)-1(S)-ethyl-3a(R),4,5(R),7a(R)-tetrahydroindan-5-yl]-1(E), 3(E)-butadienyl-tetrahydropyran-2-acetic acid. The antibiotic is produced by a Streptomyces sp. X-14547 microorganism, a culture of which has been deposited under designation number NRRL 8167 at the Agricultural Research Service. The X-14547 antibiotic has the following structural formula:

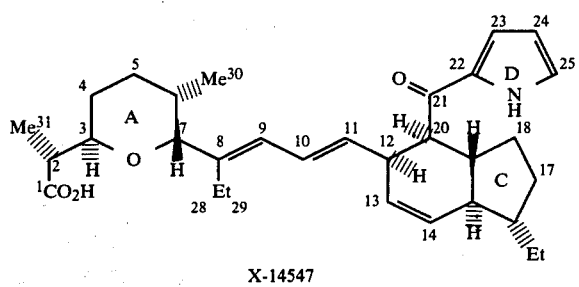

X-14547

Further details of the characteristics of the X-14547 antibiotic and processes for its production and recovery are disclosed in U.S. Pat. No. 4,100,171 to Westley et al, in U.S. Pat. No. 4,161,520 to Osborne et al, and in the articles by Liu et al, *J. Antibiotics* 32, 95–99 (1979) and Westley, *J. Antibiotics* 32, 100–107 (1979).

The pyrrole ether antibiotic known under the code designation A-23187 (also known as calcimycin) is the subject of U.S. Pat. No. 3,923,823 to Gale et al. The patent discloses that the A-23187 antibiotic has an appreciable affinity for $Cd++$, moderate affinity for $Ni++$, $Zn++$, $Co++$ and $Be++$, and no apparent affinity for $Hg++$ and suggests that because of its preferential binding of certain cations, the antibiotic can be employed in applications wherein the selective removal of particular cations is desired. It was reported by Pfeiffer et al, *Biochemistry*, Volume 15, Number 5, 935–943 (1976) that an A-23187 complex of manganese, as well as A-23187 complexes of other divalent cations, was used to investigate the selectivity of the antibiotic for divalent cations over monovalent cations. See also, Pfeiffer et al, *Biochemistry*, Volume 13, Number 19, 4007–4014 (1974). However, there is no disclosure of a specific utility for the manganese complex of A-23187 in the above article. The use of the free acid or calcium salt of the A-23187 antibiotic in a method of enhancing the contractile force of the mammalian heart muscle in a warm-blooded mammal is disclosed in U.S. Pat. No. 3,985,893 to Holland et al.

The A-23187 antibiotic is produced by culturing a *Streptomyces chartreusis* microorganism. A culture of this microorganism has been deposited in the collection of the Agricultural Research Service under accession number NRRL 3882. The A-23187 antibiotic has the structural formula:

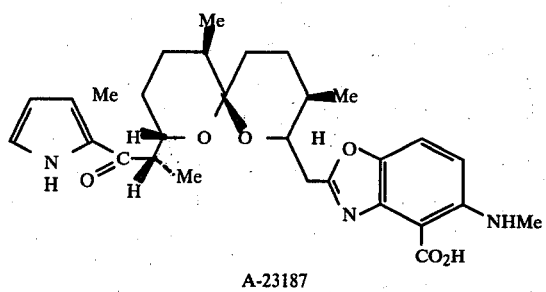

A-23187

Further details of the characteristics of the antibiotic and processes for its production and recovery are set forth in U.S. Pat. No. 3,923,823 to Gale et al.

The glycolic monovalent monoglycoside polyether antibiotics include etheromycin (Westley Class 1b). The antibiotic etheromycin (also known as C20-12 and CP 38295) has the chemical structure:

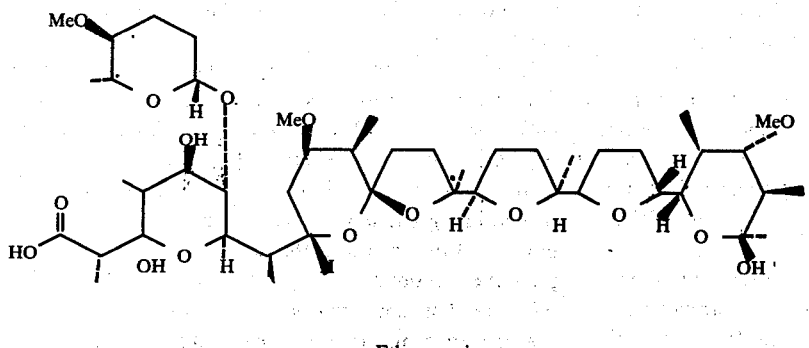

Etheromycin

This structure was published by Mitani et al in *J. Antibiotics* 31, 750–755 (1978) who also noted that etheromycin is the same as the T-40517 antibiotic. According to Westley, *Ad. Appl. Microbiology* 22, 177–223 (1977), etheromycin is produced from the *Streptomyces hygroscopicus* microorganism, a culture of which is deposited under number ATCC 31050 at the American Type Culture Collection. Additional details concerning the etheromycin antibiotic can be found in the previously mentioned U.S. Pat. No. 4,129,578 to Celmer et al.

Those polyether antibiotics for which structural information is not yet available, and which may be used to make the novel manganese complexes of the subject invention include ionomycin; aabomycin; disnerycin; duamycin; BL-580; K-41; SF-1195; M-4164A; A-32887; 30,504RP; 38,986; 44,161; 47,433; 47,434; and 47,224. Available information about these antibiotics is presented below.

The antibiotic ionomycin is the fermentation product of the *Streptomyces conglobatus* sp. nov. trejo microorganism which has been deposited under accession number ATCC 31005 at the American Type Culture Collection. The antibiotic has been characterized by Liu et al, *J. Antibiotics* 31, 815–819 (1978) which also exhibits a suitable method for the preparation of the antibiotic. The ionomycin antibiotic is also the subject of U.S. Pat. No. 3,873,693 to Meyers et al.

The isolation and characterization of the polyether antibiotic K-41 was reported by Tsuji et al, *J. Antibiotics* 29, 10–14 (1976). The antibiotic is produced from a strain of *Streptomyces hygroscopicus* microorganism deposited at the Fermentation Research Institute, Chiba, Japan, with deposit number FERM-P 1342. The above article reports that the antibiotic is the subject of Japanese Patent 49-14692 (1974). A method utilizing the antibiotic K-41 in protecting plants from mites is disclosed in U.S. Pat. No. 4,148,881 to Ishiguro.

U.S. Pat. No. 3,812,249 to J.H.E.J. Martin et al is directed to the polyether antibiotics BL-580 α and β. These antibiotics are products of a *Streptomyces hygroscopicus* microorganism which has been deposited at the Agricultural Research Service under deposit number NRRL 5647. The above-mentioned patent discloses suitable methods for the preparation of the BL-580 antibiotic. U.S. Pat. No. 4,132,779 to Hertz et al discloses the antibiotic BL-580 zeta which is produced by a mutant strain of *Streptomyces hygroscopicus* derived by treatment of a natural section, single colony isolate of *Streptomyces hygroscopicus* NRRL 5647 with N-methyl-N'-nitro-N''-nitrosoguanidine. A culture of the mutant strain has been deposited at the Agricultural Research Service under accession number NRRL 11108.

The polyether antibiotic aabomycin X was recently reported in the Supplement to "Index of Antibiotics from Actinomyces" by Dr. Hamao Umezawa, *J. Antibiotics* 32, 79–51 (1979) and is also apparently the subject of Japan Kokai No. 77-90697 filed July 30, 1977, in the name of Shibata, et al. The antibiotic is produced by the fermentation of the microorganism *Streptomyces hygroscopicus* subsp. *aabomyceticus* 325–17 which has been deposited at the American Type Culture Collection under deposit number ATCC 21449. The microorganism produces an antibiotic mixture which includes the factors aabomycin X and aabomycin A. The antibiotic aabomycin A is the subject of U.S. Pat. No. 3,657,422 to Misato et al.

The antibiotic duamycin was described in Japanese Pat. No. 26719 (1970) to Kaken-Kagaku, the patent being abstracted in *Chemical Abstracts* 74, 21895p (1971). The antibiotic SF-1195 was disclosed in Japanese Patent No. 49-132212 (1974) to Sawada et al. Disnerycin was mentioned in U.S. Pat. No. 4,159,322 to Cloyd as being a polycyclic ether antibiotic of the same class as monensin, nigericin, grisorixin, salinomycin, narasin and lasalocid. The antibiotic identified as M-4164A was described in Japan Kokai Pat. No. 50-12294 (1975) to Toyama et al.

The polyether antibiotic designated as Compound 38,986 is disclosed in U.S. Pat. Nos. 4,022,885 and 4,048,304 to Celmer et al. The antibiotic is the product of a *Streptomyces flaveolus* microorganism, a culture of which has been deposited in the American Type Culture Collection and given designation ATCC 31100.

The polyether antibiotic Compound 44,161 is produced by cultivating a strain of *Dactylosporangium salmoneum* Routien sp. nov., cultures of which have been deposited at the American Type Culture Collection under accession numbers ATCC 31222, 31223 and 31224. Additional details regarding this antibiotic are contained in U.S. Pat. No. 4,081,532 to Celmer et al.

The antibiotic A-32887 is the subject of U.S. Pat. Nos. 4,132,778 and 4,133,876 to Hamill et al. As is described in these patents, the A-32887 antibiotic is closely related to the K-41 antibiotic and is produced by culturing a strain of *Streptomyces albus* which has been deposited under designation NRRL 11109 at the Agricultural Research Service.

The two polyether antibiotics disclosed in U.S. Pat. No. 4,148,882 to Celmer et al were given the designations Compounds 47,433 and 47,434. These antibiotics are produced by a species of *Actinomadura macer* Huang sp. nov., a culture of which has been deposited at the American Type Culture Collection and given the designation number ATCC 31286.

U.S. Pat. No. 3,989,820 to Florent et al is directed to the antibiotic 30,504RP which is produced by culturing a microorganism called *Streptomyces gallinarius* DS 25881, a culture of which has been deposited at the Agricultural Research Service under number NRRL 5785.

The polyether antibiotic given the designation Compound 47,224 is produced by a strain of a *Streptomyces hygroscopicus* microorganism. As is disclosed in U.S. Pat. No. 4,150,152 to Celmer et al, the microorganism strain capable of producing Compound 47,224 has been deposited at the American Type Culture Collection with the accession number ATCC 31337.

While the above descriptions of the various known polyether antibiotics have generally identified the antibiotics as being single compounds, it should be recognized that at least some of the polyether antibiotics are produced as an antibiotic complex of structurally related factors containing varying proportions of each factor. As an example, the structure for lasalocid set forth previously is lasalocid factor A which is produced in combination with factors B, C, D and E in ratios depending upon fermentation conditions. Homologs of lasalocid A are disclosed in U.S. Pat. No. 4,168,272 to Westley. An isomeric form of lasalocid is also known from U.S. Pat. No. 3,944,573 to Westley. In addition, monensin is produced with factors B and C as reported by Westley, *Adv. Appl. Microbiology* 22, 200 (1977) and narasin is produced with factors A, B and D as is set forth in U.S. Pat. No. 4,038,384 to Berg et al. It should, therefore, be realized that the present invention comprehends the manganese complexes of the various factors of the polyether antibiotics whether in combination with other factors or in their isolated form as well as their use in promoting growth, enhancing feeding efficiency and treating coccidial infections in poultry, and in stimulating cardiovascular function in animals.

Furthermore, manganese complexes of derivatives of the previously mentioned polyether antibiotics are also within the scope of the present invention. For example, various derivatives of the lasalocid antibiotic are known from U.S. Pat. No. 3,715,372 to Stempel et al. In addition, derivatives of monensin are disclosed in U.S. Pat. No. 3,932,619 to Brannon et al which is directed to a metabolite produced from monensin, U.S. Pat. No. 3,832,258 to Chamberlin which is directed to the deshydroxymethyl derivative of monensin and U.S. Pat. Nos. 4,141,907 and 4,174,404 to Nakatsukasa et al are directed to deoxynarasin. Therefore, as used herein, the specific name of the polyether antibiotic, e.g. lasalocid, encompasses all of the factors of the antibiotic, e.g. lasalocid A, B, C, D and E, as well as isomers thereof, e.g. iso-lasalocid, and derivatives thereof.

For further particulars as to characteristics and methods for the preparation of certain of the above polyether antibiotics, reference is made to U.S. Pat. No. 3,995,027 to Gale et al and the patents cited therein and to U.S. Pat. No. 3,794,732 to Raun and the patents and articles cited therein.

It is also within the scope of the present invention that the novel manganese complexes of the polyether antibiotics described herein can be used in conjunction with other active ingredients which are also useful for challenging coccidial infections in poultry and/or for promoting growth and enhancing feed efficiency in poultry. For example, the manganese complexes of polyether antibiotics may have an enhanced effect when used in combination with metichlorpindol. The use of metichlorpindol with monensin for treatment of poultry coccidiosis is described in U.S. Pat. No. 4,061,755 to McDougald. Compositions containing certain designated polyether antibiotics and a pleuromutilin derivative which are useful in treating poultry coccidiosis are disclosed in U.S. Pat. No. 4,148,890 to Czok et al.

To the extent necessary, the above-mentioned patents and literature articles mentioned in describing the various known polyether antibiotics and their uses are incorporated herein by reference.

GENERAL DESCRIPTION OF SYNTHESIS

In accordance with the present invention, the polyether antibiotic, generally in the form of its alkali metal, alkaline earth metal or ammonium salt, is treated in situ in the fermentation broth or beer by adding to the antibiotic containing broth a water-soluble manganese salt. Addition of such a water-soluble manganese salt promotes the formation of a manganese complex of the polyether antibiotic. Such a manganese complex of the antibiotic, along with manganese complexes formed with residual nitrogen-containing compounds in the broth such as amino acids, polypeptides, and proteins, are insoluble in the fermentation broth liquid.

The manganese ions from the added manganese salt apparently form coordination bonds with the oxygen atoms of the sparingly soluble polyether antibiotic. For example, the structure of the manganese complex of lasalocid is believed to be represented by the following:

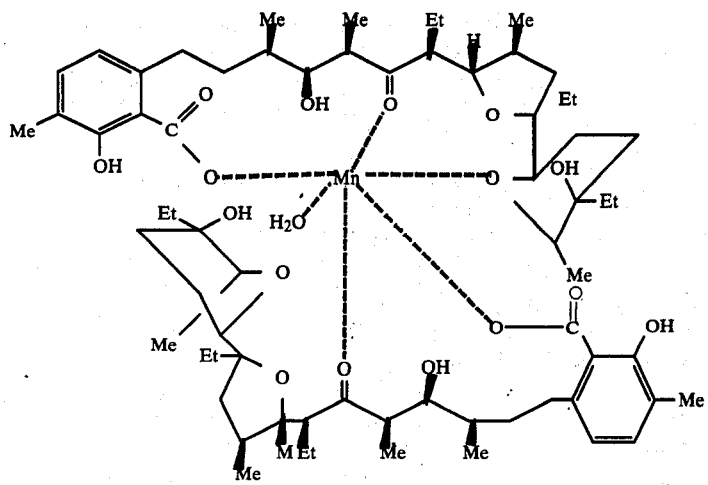

Manganese Lasalocid Monohydrate

On the basis of the formation constants with ligands such as citric acid, lactic acid and tartaric acid, it is believed that manganese ions form stronger bonds with oxygen-containing compounds than do ions such as $Mg^{++}$, $Ca^{++}$, $Ba^{++}$, $Na^+$ and $K^+$.

The manganese salt added to the fermentation broth can be chosen from various water-soluble salts which ionize in the fermentation broth. Such salts include, for example, manganese chloride, manganese nitrate, manganese acetate, etc. Water-soluble manganese salts are generally those which can be dissolved to the extent of about 1 percent by weight or more in water at 20° C. For maximum production of the desired manganese complexes, the water-soluble manganese salt should be added to the fermented broth in an amount which is sufficient to fill substantially all of the possible manganese coordination sites of the proteins, polypeptides, amino acids and related compounds, in addition to substantially all of the available coordination sites of the antibiotic present. This is necessary because in general, nitrogen atoms in the polypeptides, amino acids, etc., form stronger coordination bonds with manganese than do the oxygen atoms in the polyether antibiotic. Generally, therefore, manganese salt is added to the fermentation broth in an amount sufficient to provide a manganese content of from about 3 to 12 percent, and preferably, from about 5 to 10 percent by weight of the dried precipitate recovered from the fermentation broth as hereinafter more fully described.

The amount of soluble manganese salt to be added will depend on the amount of nutrients added to the fermentation broth during the course of the fermentation. The actual amount of soluble manganese salt to be added to the broth obtained from a given mash bill can be determined by simple laboratory precipitations followed by manganese analyses on the dried precipitates. When, for example, the preferred manganese chloride salt is employed to form the desired manganese antibiotic complex, advantageously from about 8 to 18 gallons of a 43.5 weight percent manganese chloride solution (sp. gr. 1.499), can be added to 1000 gallons of fermentation broth.

To form the manganese antibiotic complex in the fermentation broth, pH of the broth is advantageously adjusted to about 6.5 to 7.5, and preferably, to about 6.8 to 7.2 after addition of the soluble manganese salt to the fermentation broth.

The insoluble manganese complexes formed upon addition of manganese salt can be readily separated from the fermentation broth or beer by conventional filtration or centrifugation techniques. In this manner, a wet biomass containing the manganese antibiotic complex is realized. This wet biomass is resistant to wild fermentations because of its relatively high manganese content. The wet biomass so obtained is easily dried by spray drying or drum drying procedures, and this manganese antibiotic-containing dried product can then be used as a feed additive per se. If the antibiotic content of the fermentation beer is lower than desired after completion of the fermentation, crude antibiotic in its sodium salt form can be added to the fermentation beer prior to the addition of the soluble manganese salt. In this manner, the antibiotic content of the biomass composition to be separated from the broth can be increased. To be suitable as a feed additive, the dried biomass preferably contains at least about 5 percent by weight of the manganese antibiotic complex, advantageously from about 10 percent to 50 percent by weight of the manganese antibiotic complex.

Recovery of the manganese antibiotic complexes of the present invention in the manner described herein provides several important advantages over known antibiotic preparation and recovery processes. The present process, for example, provides a means for recovering relatively high yields of antibiotic in a salable feed additive product. Further, the use of expensive extraction solvents and the cost associated with the process losses of such solvents are avoided. The present process also permits recovery of salable feed values present in the mycelium of the Streptomyces microorganism used to produce the antibiotic. The present process further reduces the cost of waste disposal operations needed in previous processes to deal with the mycelial mat produced during fermentaton. Use of this mat as part of the feed additive product, in fact, reduces the cost of the carrier for the antibiotic material being marketed.

The dried, antibiotic-containing biomass recovered from the fermentation broth as hereinbefore described can be added to conventional poultry feed compositions as a coccidiostatic and growth-promoting agent. Such feed compositions generally contain whole or ground cereal or cereal byproducts as an essential nutrient. The feed compositions can also contain such optional additional materials as animal byproducts, e.g., bone meal, fish meal, etc., carbohydrates, vitamins, minerals and the like. The manganese antibiotic complexes of the present invention are generally employed in the feed compositions to the extent of from about 50 grams per ton to 200 grams per ton, preferably from about 75 grams per ton to 125 grams per ton.

As was mentioned previously, the manganese complexes of polyether antibiotic according to the present invention may also be utilized for the stimulation of cardiovascular functions and particularly in the treatment of ailments such as cardiogenic shock, septic shock and congestive heart failure. Preferably, the manganese complexes are utilized for these purposes in a purified form and are administered either orally or parenterally to a patient requiring treatment. Oral administration is particularly preferred for long term treatment of chronic diseases such as congestive heart failure while parenteral administration is preferred for emergency treatment such as in the treatment of shock and of acute heart failure.

Purification of the manganese complexes of the present invention so that the complexes are more suitable for administration to humans can be accomplished in a variety of manners. A presently preferred method for purification of the manganese complexes from the recovered feed grade manganese complex includes the steps of, after treatment of the fermentation beer with a soluble manganese salt, acidifying the water slurry of the manganese complex with strong mineral acid such as sulfuric acid to produce a relatively low pH, e.g. a pH below about 4, preferably about 2 to about 3, and then extracting the acid form of the polyether antibiotic from the slurry into a substantially water-insoluble organic solvent such as butyl acetate.

Thereafter, a lower aliphatic alcohol such as methanol is added to the organic solvent containing the polyether antibiotic. The volume of alcohol added is generally less than or about equal to the volume of organic solvent, preferably about 0.25 to about 1.0 volumes alcohol to about 1.0 volume of organic solvent. A soluble manganese salt such as manganese chloride dissolved in the same lower aliphatic alcohol is then slowly added with vigorous agitation to the organic solvent-alcohol mixture containing the polyether antibiotic. Preferably, about 0.5 to 1.0 volumes of the alcohol containing the manganese salt are added per volume of mixture. The amount of manganese salt added should be sufficient to convert essentially all of the contained antibiotic to its manganese complexed form. The formed manganese complexes are then filtered from the mixture, thoroughly washed and dried.

If greater purification of the manganese complex is desired, the above procedure can be modified to include further purification steps. One such modification is, prior to the addition of the lower aliphatic alcohol, adding an aqueous solution containing an alkali metal hydroxide such as potassium or sodium hydroxide to the organic solvent containing the polyether antibiotic so that the antibiotic is extracted into the aqueous solution. The antibiotic is then re-extracted into the same organic solvent or a different water-insoluble organic solvent such as methyl tertiarybutyl ether after acidification. These steps of the modified procedure can be repeated as many times as desired until the proper degree of purification is achieved. Thereafter, the polyether antibiotic is contacted with the lower aliphatic alcohol and the previously mentioned procedure continued so as to yield the purified manganese complex of the polyether antibiotic.

In the above description of the purification procedure and modification thereof, the amount of each of the media, i.e., the organic solvent, aliphatic alcohol, aqueous solution, etc., relative to the others when conducting the procedure may vary considerably, the primary considerations being that sufficient media be utilized to obtain a satisfactory yield of the manganese complex balanced against the cost of the media and the capacity of the available equipment. Generally, the amount of a particular medium used to treat another medium in any of the steps of the above procedure is about 0.1 to 10 volumes, preferably about 0.5 to about 5 volumes, for each volume treated.

Certain advantages are realized by the above procedure where the purified manganese complexes are recovered from the feed grade complexes as opposed to recovery of the purified complexes from virgin mycelia. Among others, the feed grade complexes are filtered relatively easily from the fermentation beer whereas filtering of virgin mycelia is very slow and thus time-consuming. In addition, the feed grade complexes tend to be more concentrated and thus less organic solvent is required in conducting the purification procedure of volume loss of solvent will be reduced.

DESCRIPTION OF USES

The manganese complexes of the present invention may be formulated with conventional inert pharmaceutical carrier or adjuvant materials into dosage forms which are suitable for oral or parenteral administration to stimulate cardiovascular function. Such dosage forms include tablets, suspensions, solutions, hard or soft capsules, dragees and the like. The selection of suitable materials which may be used in formulating the active manganese complexes into oral and parenteral dosage forms will be apparent to persons skilled in the art. Such materials, either inorganic or organic in nature, should be of pharmaceutically acceptable quality, free from deleterious impurities and may include, for example, water, dimethylsulfoxide, gelatin albumin, lactose, starch, magnesium stearate, preservatives, stabilizers, wetting agents, emulsifying agents, salts for altering osmotic pressure, buffers, etc. which can be incorporated, if desired, into such formulations.

The quantity of manganese complex which may be present in any of the above described dosage forms generally varies from 10 to 100 mg per unit dosage. The dosage administered to a particular patient is variable, depending upon the clinician's judgment using the criteria of the condition and the size of the patient, the potency of the manganese complex and the patient's particular response thereto. An effective dosage amount of the manganese complex can, therefore, only be determined by the clinician utilizing his best judgment on the patient's behalf. Generally, parenteral doses should be from about 20 mg to about 50 mg for the average size person. Smaller persons or larger persons may require adjustments due to body size. Oral doses, usually capsules, but tablets can be used, generally contain about twice the parenteral dose. The frequency of the administration of the manganese complex depends generally upon the patient's condition and the desired response from the patient. Chronically ill patients may require administration every 2 to 3 hours or once a day, depending on the severity of the disease and the patient's particular response to treatment. Emergency patients generally require only one dose of the manganese complex, particularly those patients in shock.

When administered to a patient requiring treatment, the manganese complexes of the present invention generally have a positive inotropic effect with little or no chronotropic effects and display minimal, if any, adrenergic action, have a rapid onset of action, require a small effective dose, are non-toxic at the effective doses, have a satisfactory duration of action, display a return to the original predrug values of cardiovascular activity, and exhibit continued generally identical responses to subsequently repeated identical dosages.

Illustrated in the following examples are preparation and recovery methods for the manganese complexes of polyether antibiotics as well as feed and feed additive compositions including these manganese complexes and their usefulness as coccidiostats and growth-promoting agents for food-producing animals such as cattle, sheep, swine and poultry, and, in addition, pharmaceutical compositions including these manganese complexes and their usefulness in stimulating cardiovascular function. These examples are in no way to be considered limiting of the present invention to compositions, ingredients, and processes involving that particular material.

EXAMPLE I

A. Fermentation

About 450 ml of inoculum of *Streptomyces lasaliensis* culture No. NRRL 3382R, obtained from the Agricultural Research Service is introduced into 9,000 ml of fermentation medium of the following composition:

| Soybean Flour | 2% |
| --- | --- |
| Brown Sugar | 2% |
| Corn Steep Liquor | 0.5% |
| K$_2$HPO$_4$ | 0.1% |
| Hodag Antifoam K-67 | 0.05% |
| Water | Balance |
| | 100.00% |

The fermentation is conducted in a 20-liter, stainless steel fermentor using the conditions listed below.
1. Amount of medium—9.45 liters.
2. Temperature—28° C.
3. Air Flow—9.0 liters per minute.
4. Mechanical agitation—One 13-cm diameter impeller rotating at 600 RPM.
5. Back pressure—about 16.7 psig.
6. Time of fermentation—72 hours.

At the end of the fermentation the lasalocid assay of the beer is 1.5 g per liter.

B. Recovery

Since the assay of the beer for lasalocid is low compared to assays commonly obtained for antibiotics, the beer is spiked with crude lasalocid which has been obtained by extracting with butyl acetate a commercial product containing approximately 81 grams of sodium lasalocid per pound.

Twenty-five grams of crude sodium lasalocid (78.5% lasalocid) dissolved in 150 ml of methanol are added to 2000 ml of beer under constant agitation. After thorough agitation, 12.5 ml of a manganese chloride solution (0.25 g Mn per ml) are slowly added with agitation to the fermented beer. The pH is adjusted to a value in the range 7.0–7.4.

After the treated beer has been agitated for about 30 minutes it is filtered, without filter aid, on a Buckner funnel using No. 1 Whatman filter paper. The filtration proceeds rapidly to give a firm cake which is dried in an oven. The final dried product weighs 57 grams and has an assay of 32.7% lasalocid.

The calculated recovery from beer to dried product is 82.5% derived from the following formula.

$$\frac{0.327 \times 57}{2 \times 1.5 + 25 \times 0.785} \times 100\% = 82.4\%$$

EXAMPLE II

Objective

To determine the efficacy of the new manganese lasalocid complex as an anticoccidial compound for poultry, manganese lasalocid is tested in comparison with Coban (monensin sodium) in chickens which are challenged by *Eimeria tenella*.

| Test Animals: | Species: Avian | Total Number: | 24 birds/ treatment | Initial Age: | 14 days |
| --- | --- | --- | --- | --- | --- |
| Breed: | Hubbard White Mountain | | Sex: | Male | Initial 330 g Weight: |
| Test Materials | | | | | |
| Manganese lasalocid - 32.7% pure by weight | | | | | |
| Coban (monensin sodium) - Lot No. X31211 | | | | | |

Test Procedure

1. At 14 days of age chicks are weighed and assigned to groups. Immediately after groups are formed (composed of 12 chicks each) chicks are started on their respective medicated feed ration. Each treatment group is replicated twice for a total of 24 birds per group.

2. Seventy-two hours after the initiation of medication, birds are orally inoculated with approximately 100,000 *Eimeria tenella* oocysts suspended in a 1 cc dose.

3. Controls consist of an infected non-medicated group, a non-infected group and an infected group treated with Coban.

4. Criteria for evaluation are
a. Morbidity (4th–6th day);
b. Mortality (4th–7th day);
c. Incidence of bloody droppings (4th–6th day);
d. Body weight gain;
e. Feed per gain;
f. Postmortem lesions.

Treatment Groups

| Pen | Treatment |
| --- | --- |
| 4, 9 | Manganese lasalocid, 75 g/ton |
| 1, 6 | Manganese lasalocid, 113 g/ton |
| 5, 12 | Manganese lasalocid, 150 g/ton |
| 7, 11 | Coban, 110 g/ton |
| 3, 8 | Non-inoculated control |
| 2, 10 | Inoculated control |

Rations

Rations employed in the Example II testing are summarized in Table 1.

TABLE 1

Chick Starter (corn)

| | |
|---|---|
| % Protein 23.0 | % Calcium .98 |
| M.E. Kilocalories/lb 1376* | % Total phosphorus .89 |
| Ground yellow corn | 55.0 |
| Soybean meal 44% | 29.0 |
| Fish solubles | 2.0 |
| Meat and bone | 5.0 |
| Dehydrated alfalfa meal | 1.2 |
| Dried whey | 1.0 |
| Animal tallow | 4.0 |
| Dicalcium phosphate | 1.0 |
| Hubbard super-13 | 0.8 |
| Vitamin and trace mineral premix | 0.5 |
| Salt | 0.5 |
| | 100.0 |

*M.E. — Metabolizable Energy

Test Results

Results obtainable from the Example II testing demonstrate that a satisfactory challenge is obtained with *E. tenella* and that all three levels of manganese lasalocid demonstrate excellent activity against this organism. In fact the birds receiving the two lower levels of manganese lasalocid also show superiority over the controls in weight gain and in feed efficiency. Furthermore, manganese lasalocid gives results superior to those obtained with Coban in controlling *E. tenella*, in weight gain and in feed efficiency.

EXAMPLE III

An experiment is run to confirm the indication in Example II that manganese lasalocid has growth promoting properties for chickens.

Objective

To determine the efficacy of manganese lasalocid for promoting the growth and improving feed efficiency in broiler chicks.

| Test Animals: | Species:Avian | Total Number: | 60 birds/ treatment | Initial Age: | 2 days |
|---|---|---|---|---|---|
| Breed: | Hubbard White Mountain | Sex: Male | Initial Weight: 43 g | Duration of Test: | 13 days |

Two-day old broiler type chicks are placed into Petersime starter batteries and given feed and water ad libitum for the duration of the test. Chicks are divided into four treatment groups which are replicated six times with ten chicks (males) in each replication. The test period is 13 days. Pen live body weights are taken at 2, 7 and 14 days of age. Pen feed efficiency measurements are taken at 14 days of age.

Rations

Rations employed in the testing are summarized in Table 2.

TABLE 2

Chick Starter (Rye)

| | |
|---|---|
| % Protein 23.2 | % Calcium 0.98 |
| M.E. Kilocalories/lb 1260* | % Total phosphorus 0.89 |
| Ground rye | 55.0 |
| Soybean meal 44% | 29.0 |

TABLE 2-continued

Chick Starter (Rye)

| | |
|---|---|
| Fish solubles | 2.0 |
| Meat and bone meal | 5.0 |
| Dehydrated alfalfa meal | 1.2 |
| Dried whey | 1.0 |
| Animal tallow | 4.0 |
| Dicalcium phosphate | 1.0 |
| Hubbard Super-13 mineral | 0.8 |
| Vitamin and trace mineral premix | 0.5 |
| Salt | 0.5 |
| | 100 lbs |

*M.E. — Metabolizable Energy

Test Results

Results obtainable from the Example III testing demonstrate that, at levels of 50 and 100 grams per ton, manganese lasalocid greatly improves growth response and feed efficiency of young broiler chicks.

EXAMPLE IV

Objective

To compare efficacy of manganese lasalocid against lasalocid and zinc bacitracin for promoting growth and improving feed efficiency in the chick.

| Test Animals: | Species:Avian | Total Number: | 60 birds/ treatment | Initial Age: | 2 days |
|---|---|---|---|---|---|
| Breed: | Hubbard White Mountain | Sex: Male | Initial Weight: 36 g | Duration of Test: | 14 days |

Test Procedure

Two-day old broiler type chicks are placed into Petersime starter batteries and given feed and water ad libitum for the duration of the test. Chicks are randomly divided into four treatment groups which are replicated six times with ten chicks (males) in each replication. The test period was 14 days. Pen live body weights are taken at 2, 7 and 15 days of age. Pen feed efficiency measurements are taken at 15 days of age.

Treatment Groups

| Pen | Treatment | Lot No. |
|---|---|---|
| 241, 246, 249 256, 259, 264 | Control | |
| 245, 248, 251 254, 255, 262 | Lasalocid[1], 50 g/ton | P-446 E |
| 244, 247, 250 253, 258, 263 | Zinc bacitracin[2], 50 g/ton | 11207902 |
| 242, 243, 252 257, 260, 261 | Manganese lasalocid[3], 50 g/ton | Prepared by Procedure of Example I |

[1]Lasalocid — 68 g/lb (Avatec)
[2]BACIFERM — 10
[3]Manganese lasalocid — 32.7% lasalocid by wt.

Rations

The composition of the chick starter ration is given in Table 2 of Example III.

Test Results

Results obtainable from the Example IV testing show that manganese lasalocid fed at 50 g/ton will produce about a 45% increase in body weight gain compared to the control group. Under these same test conditions, lasalocid actually depressed body weight gain by about 5% compared to the control. Manganese lasalocid will produce a Feed/Gain ratio of about 1.48, or an 8.6% increase over the control, whereas lasalocid, under the same test conditions, produced a Feed/Gain ratio of 1.61 which was only 0.4% over the control.

EXAMPLE V

Administration of manganese lasalocid growth-promoting agent to cattle via cattle feed composition is ilustrated by this example. A cattle feed formulation having the following composition is prepared:

| Composition | Concentration |
| --- | --- |
| Cracked Corn | 68.5% |
| Alfalfa Meal | 5.0% |
| Ground Cobs | 10.0% |
| Soybean Meal (50% protein) | 15.0% |
| Mineral Mixture | 1.0% |
| Salt | 0.5% |
|  | 100.0% |

To such a composition is added enough of the manganese lasalocid-containing dried product of Example I to provide a feed composition containing about 100 grams of manganese lasalocid per ton of feed composition.

The manganese lasalocid-containing feed composition is fed to cattle in amounts sufficient to provide from about 5 to 100 ppm of manganese lasalocid in the rumen fluid. Administration of the manganese lasalocid material in this manner serves to promote cattle growth by enhancing the efficiency with which the cattle so treated utilize their feed.

EXAMPLE VI

The tendency of manganese lasalocid antibiotic to desirably affect acetate/propionate ratios in rumen fluid from cattle is demonstrated by means of an in vitro rumen fluid analysis procedure. Rumen fluid is obtained from a steer which has a surgically installed fistula opening into the rumen. The steer is maintained on a grain diet consisting of the feed composition set forth in Example V. A sample of rumen fluid is strained trough four layers of cheesecloth and the eluate collected. An equal amount of buffer solution with a pH of 7 is added to the rumen fluid. Ten ml of the diluted rumen fluid is placed in flasks with 500 mg of the same feed shown above which has been finely ground. Each of materials to be tested is weighed into a separate test flask. Four control flasks are also employed. All of the test flasks are incubated for 24 hours at 39° C. At the end of incubation, a pH is measured and one drop of mercuric chloride is added to each flask. The samples are centrifuged at 3000×g for 15 minutes and the supernatant is analyzed by gas chromatographic methods for volatile fatty acids.

Analyses for acetate, propionate and butyrate compounds are performed. The results are statistically compared with the results of the analyses of the control flasks. The acetic/propionic ratios are calculated for each treatment. Treatments with propionate production significantly higher than the control are evidenced in this ratio expression by lesser numbers. These treatments are then regarded as active treatments. Results of these tests are set forth in Table I immediately below.

TABLE I

Effect of Manganese Lasalocid on Acetate/Propionate Ratios of In Vitro Ruminal Fluid

| Item* | Negative Control | Positive Control Monensin 5 ppm | Lasalocid, ppm | | |
| --- | --- | --- | --- | --- | --- |
|  |  |  | 1 | 5 | 10 |
| Acetate/propionate | 1.47 | 1.04 | 1.10 | .99 | 0.95 |

*Means of seven experiments, 3 reps/treatment

The data in Table I demonstrates that the presence of manganese lasalocid in the rumen fluid can beneficially increase the production of propionate within the rumen relative to acetate production. Cattle wherein such a propionate increase occurs are more efficiently able to utilize their feed in the production of meat and milk.

EXAMPLE VII

The manganese complex of lasalocid is purified by a purification process, incorporated into a pharmaceutical composition, and is then administered to dogs to stimulate their cardiovascular function.

Purification

To a liter of fermentation beer slurry containing manganese lasalocid which was produced in a manner as set forth in Example I, sufficient concentrated sulfuric acid is added to acidify the slurry of fermentation beer to a pH of about 3.0. The slurry is then mixed with about one liter of a butyl acetate organic solvent so that the manganese lasalocid is extracted in the solvent. The organic solvent which contains the lasalocid antibiotic is then separated from the acidic aqueous beer and is mixed with about one liter of an aqueous solution of sodium hydroxide having a pH of about 9.0 so that the lasalocid antibiotic will be extracted into the aqueous alkaline solution. Upon separation of the aqueous alkaline solution from the organic solvent, about one liter of methyl tertiary-butyl ether solvent is added to the aqueous solution to re-extract the lasalocid antibiotic into the solvent. Thereafter, about 0.5 liter of methanol is first added to the solvent and then about 0.5 liter of a solution of manganese chloride in methanol is slowly added with vigorous agitation. A manganese complex of lasalocid is thereby formed in the methanol-solvent mixture which is subsequently filtered from the mixture, thoroughly washed with additional methanol and then dried. The formed manganese complex of lasalocid is suitable for administration to stimulate cardiovascular function.

Pharmaceutical Preparation

A pharmaceutical composition containing the manganese complex of lasalocid is prepared, the composition being suitable for parenteral administration.

The following ingredients are utilized to prepare a 5 ml parenteral solution:

| Manganese complex of lasalocid | 50 mg |
| --- | --- |
| Propylene glycol | 2.5 ml |
| Benzyl alcohol | 0.075 ml |
| Ethyl alcohol | 0.5 ml |
| Water | Balance |

Treatment

The above parenteral composition, or any other form of the manganese complexes of the present invention, is administered to animals, e.g. mammals such as, for instance, dogs, prophylactically for, or having a cardiovascular malfunction to stimulate their respective cardiovascular functions. The procedure utilized is similar to that set forth in U.S. Pat. No. 4,058,620 to Westley. The electrophysical and hemodynamic responses of the dogs are measured before and at various time intervals after intravenous injections of the composition. The parameters measured are myocardial force of contraction, heart rate and blood pressure. Positive inotropic effects are sought with minimal chronotropic effects being manifested in the treated animal.

EXAMPLE VIII

A manganese complex of lasalocid as purified by the procedure of Example VII is formulated into pharmaceutical tablets suitable for oral administration in stimulating cardiovascular function.

Each tablet has the following composition:

| | |
|---|---|
| Manganese complex of lasalocid | 25 mg |
| Lactose | 113.5 mg |
| Corn starch | 55.5 mg |
| Pregelatinized corn starch | 8 mg |
| Calcium stearate | 3 mg |

The tablets are made by thoroughly mixing the manganese complex, lactose, corn starch and pregelatinized corn starch, passing the mixture through a comminuting machine and then moistening the mixture with water in a mixer to produce a paste. The formed paste is screened to form granules and then dried. Calcium stearate is mixed with the dried granules and the granules compressed into tablets using a conventional tableting machine.

EXAMPLES IX-XLV

Other manganese complexes of polyether antibiotics are produced and recovered and the resultant complexes are used as coccidiostats and growth-promoting agents in food-producing animals such as cattle, sheep, swine and poultry and as pharmaceutical formulations for myocardial stimulation in animals. The antibiotics utilized in the examples are monensin, nigericin, salinomycin, narasin, noboritomycin A and B, lysocellin, grisorixin, X-206, lonoymcin, laidlomycin, SY-1, mutalomycin, alborixin, carriomycin, septamycin, dianemycin, A-204, lenoremycin, calcimycin, X-14547, A-23187, etheromycin, ionomycin, aabomycin, disnerycin, duamycin, BL-580, K-41, SF-1195, M-416A, A-32887, 30,504RP, 38,986, 44,161, 47,433, 47,434 and 47,224.

Each of the manganese complexes is produced and recovered by a process similar to that set forth in Example I except that the appropriate microorganism is utilized instead of the lasalocid producing microorganism. Specific processes for obtaining the named antibiotics are set forth above.

Some of the recovered manganese complex of each antibiotic is utilized in a feed composition and fed to healthy and coccidiosis-infected groups of food-producing animals such as cattle, sheep, swine and poultry while the remainder is purified in a process similar to that set forth in Example V. In accordance with the compositions and processes of the present invention, each of the manganese complexes, alone or in combination, is then administered to dogs to provide myocardial stimulation, or in treatment for coccidiosis in poultry, or for growth promotion in food-producing animals such as cattle, sheep, swine and poultry for growth promotion and as coccidiostats.

When fed to ruminants, the recovered manganese complex of each antibiotic is formulated into a feed composition similar to the composition set forth in Example II and fed to cattle in amounts sufficient to provide from about 5 to 100 ppm of the manganese complex in the rumen fluid during rumination. Positive effects are realized for each polyether antibiotic in its manganese complexed form in promoting growth and feed efficiency in cattle. Similar results were also obtained in myocardial stimulation in mammals.

While the present invention has been described it is understood that numerous modifications may be made by those skilled in the art without actually departing from the spirit and scope of the invention.

What is claimed is:

1. A method for producing a manganese complex of a polyether antibiotic, said method comprising:
   (a) fermenting a nutrient broth inoculated with a Streptomyces microorganism capable of producing by growth in the broth a polyether antibiotic for a period of time and under suitable fermentation conditions in order to produce said polyether antibiotic in said fermentation broth; and
   (b) providing in said antibiotic containing fermented broth a water-soluble manganese salt in an amount sufficient to form a manganese complex of said polyether antibiotic, which complex is insoluble in the fermented broth.

2. The method of claim 1 further including the step of recovering said insoluble manganese complex from said fermented broth.

3. The method of claim 1 wherein the fermentation of the inoculated broth is conducted at a temperature of from about 25° C. to 35° C. and at a pH of from about 6.5 to 7.5.

4. The method in accordance with claim 2 or 3 wherein the manganese salt is added to the fermented broth and is selected from manganese chloride and manganese sulfate.

5. The method of claim 2 or 3 wherein the Streptomyces microorganism employed is *Streptomyces lasaliensis* and the polyether antibiotic complex produced is manganese lasalocid.

6. The method of claim 2 or 3 wherein the Streptomyces microorganism employed is *Streptomyces cinnamonensis* and the polyether antibiotic complex produced is manganese monensin.

7. The method of claim 2 or 3 wherein the Streptomyces microorganism employed is *Streptomyces longwoodensis* and the polyether antibiotic complex produced is manganese lysocellin.

8. The method of claim 2 or 3 wherein the Streptomyces microorganism employed is selected from the following list to produce the manganese polyether antibiotic specified below:

| | |
|---|---|
| S. sp. X14547 | Manganese X-14547 |
| S. chartreusis | Manganese A-23187 |
| S. hygroscopicus sp. | Manganese etheromycin |
| S. hygroscopicus | Manganese carriomycin |

-continued

| | |
|---|---|
| S. albus sp. | Manganese salinomycin |
| S. albus sp. | Manganese alborixin |
| S. albus sp. | Manganese SY-1 |
| S. aureofaciens | Manganese narasin |
| S. noboritoensis | Manganese noboritomycin A & B |
| S. griseus | Manganese grisorixin |
| S. ribosidicus | Manganese lonomycin |
| S. mutabilis | Manganese mutalomycin |
| S. eurocidicus var. asterocidicus | Manganese laidlomycin |

9. A method in accordance with claim 2 wherein the insoluble manganese antibiotic complex is recovered from said fermented broth as part of a biomass which additionally contains insoluble manganese complexes of residual nitrogen-containing compounds present in the fermentation broth.

10. A method in accordance with claim 9 wherein water soluble manganese salt is added to the fermented broth in an amount sufficient to provide a manganese content of from about 3 to 12 percent by weight on a dry basis in the biomass recovered from said fermentation broth.

11. A method in accordance with claim 1 further including the steps of:
(c) acidifying the fermented broth containing the insoluble manganese complex to form the acidic form of the polyether antibiotic;
(d) extracting the polyether antibiotic from the broth into a water-insoluble organic solvent;
(e) adding a lower aliphatic alcohol to the organic solvent containing the polyether antibiotic, the alcohol containing a soluble manganese salt in an amount sufficient to form a manganese complex of the polyether antibiotic; and
(f) recovering the formed manganese complex of the polyether antibiotic from the organic solvent-alcohol mixture.

12. A method in accordance with claim 11 wherein the aliphatic alcohol is methanol.

13. A method in accordance with claims 11 or 18 wherein the organic solvent is butyl acetate.

14. A method in accordance with claim 11 wherein the fermentation broth is acidified to a pH of 4.0 or less.

15. A method in accordance with claim 11 wherein the manganese salt used in step (e) is manganese chloride.

16. A method in accordance with claim 11 further including the step of adding an aliphatic alcohol to the organic solvent containing the polyether antibiotic prior to step (e).

17. A method in accordance with claim 11 further including the steps of extracting the polyether antibiotic from the organic solvent into an aqueous alkaline solution and then extracting the polyether antibiotic from the aqueous alkaline solution into a second water-insoluble organic solvent.

18. A method in accordance with claim 17 wherein the aqueous alkaline solution contains a metal hydroxide selected from the group consisting of sodium hydroxide and potassium hydroxide.

19. A method in accordance with claim 17 wherein the second water-insoluble organic solvent is selected from the group consisting of butyl acetate and methyl tertiary-butyl ether.

* * * * *

UNITED STATES PATENT AND TRADEMARK OFFICE
CERTIFICATE OF CORRECTION

PATENT NO. : 4,478,935          Page 1 of 5
DATED : October 23, 1984
INVENTOR(S) : Williams et al.

It is certified that error appears in the above-identified patent and that said Letters Patent is hereby corrected as shown below:

Col. 1, line 29, "Streptomyces" should be in italics.

Col. 2, line 22, "Streptomyces" should be in italics;
line 33, "at" should be -- et --;
line 41, "cerriomycin" should be -- carriomycin --.

Col. 3, line 32, "Streptomyces" should be in italics;
lines 62 and 63, "Streptomyces" should be in italics.

Col. 6, lines 32 and 33, the phrase "which is on deposit at Agricultural Research Service under the number NRRL" should not be in italics but rather should be in standard type.

Cols. 5 and 6, between lines 37 and 47, the formula should be as follows:

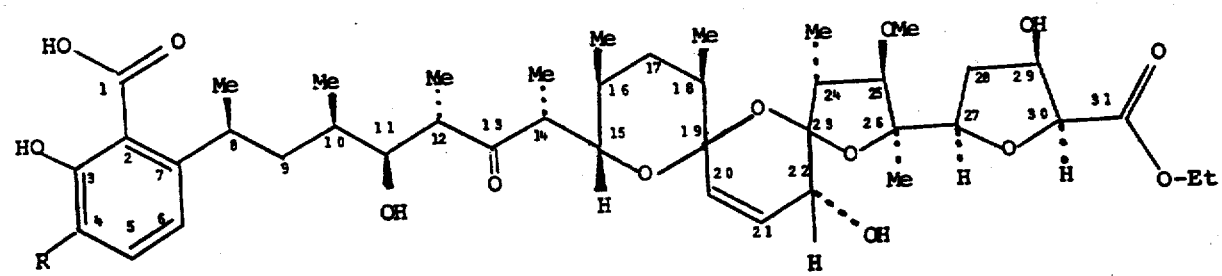

UNITED STATES PATENT AND TRADEMARK OFFICE
CERTIFICATE OF CORRECTION

PATENT NO. : 4,478,935

DATED : October 23, 1984

INVENTOR(S) : Williams et al.

It is certified that error appears in the above-identified patent and that said Letters Patent is hereby corrected as shown below:

Col. 7, between lines 53 and 61, the formula should be as follows:

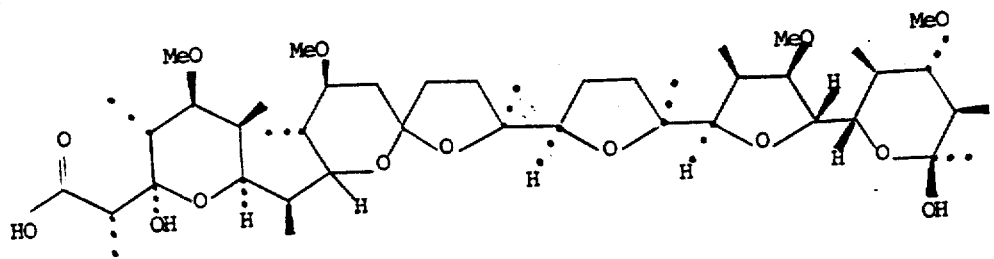

Col. 14, between lines 44 and 59, the formula should be as follows:

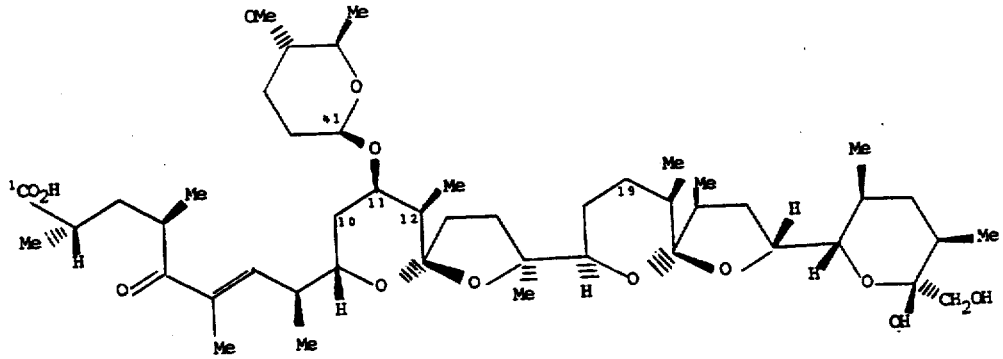

UNITED STATES PATENT AND TRADEMARK OFFICE
CERTIFICATE OF CORRECTION

PATENT NO. : 4,478,935
DATED : October 23, 1984
INVENTOR(S) : Williams et al.

It is certified that error appears in the above-identified patent and that said Letters Patent is hereby corrected as shown below:

Col. 15, between lines 4 and 15, the formula should be as follows:

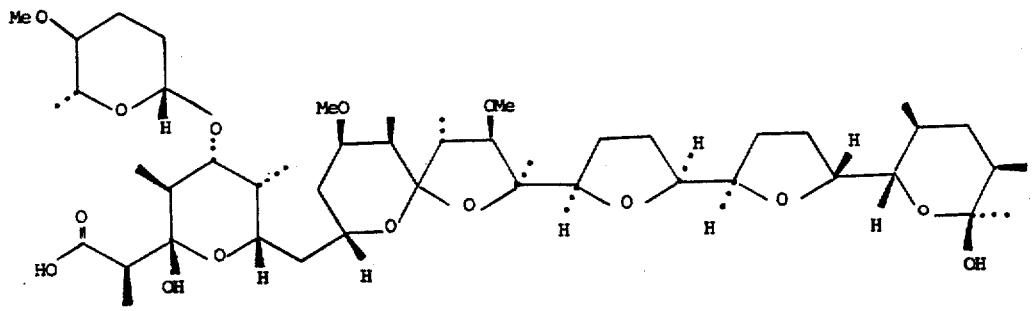

Col. 17, between lines 1 and 12, the formula should be as follows:

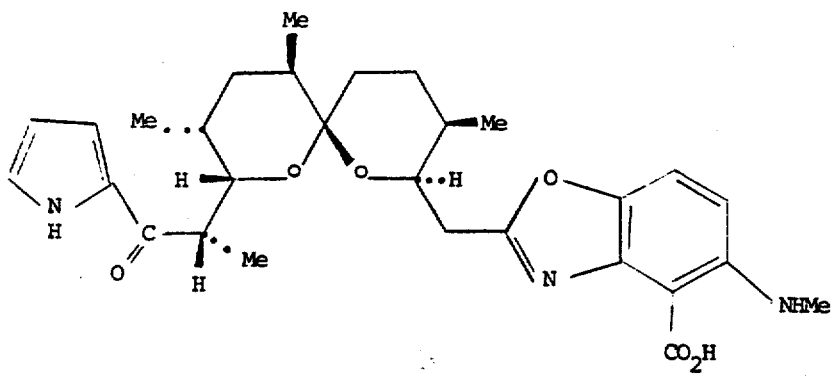

UNITED STATES PATENT AND TRADEMARK OFFICE
CERTIFICATE OF CORRECTION

PATENT NO. : 4,478,935

DATED : October 23, 1984

INVENTOR(S) : Williams et al.

It is certified that error appears in the above-identified patent and that said Letters Patent is hereby corrected as shown below:

Col. 17, between lines 21 and 34, the formmula should be as follows:

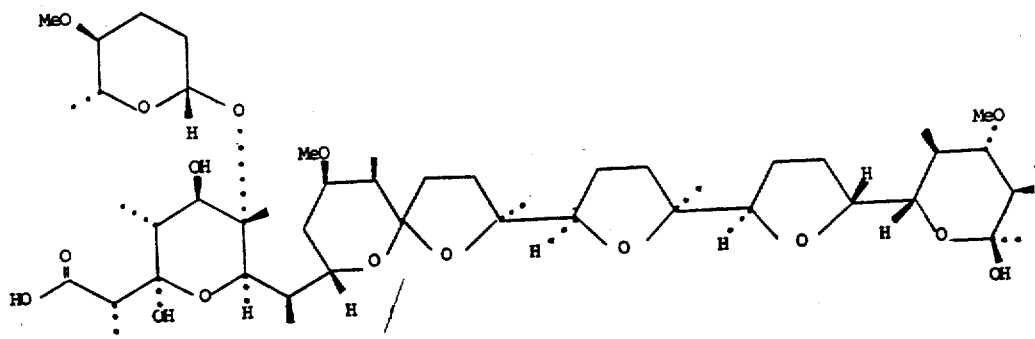

Col. 24, line 32, "of" should be -- and --.

Col. 27, lines 52 and 53, "ad libitum" should be in italics.

UNITED STATES PATENT AND TRADEMARK OFFICE
CERTIFICATE OF CORRECTION

PATENT NO. : 4,478,935　　　　　　　　　　　　　　Page 5 of 5
DATED : October 23, 1984
INVENTOR(S) : Williams et al.

It is certified that error appears in the above-identified patent and that said Letters Patent is hereby corrected as shown below:

Col. 28, lines 37 and 38, "ad libitum" should be in italics.

Col. 29, line 40, "in vitro" should be in italics.

Col. 31, line 54, "M-416A" should be -- M-4164A --.

Col. 34, Claim 13, line 1, "18" should be -- 12 --.

Signed and Sealed this

Twenty-ninth Day of October 1985

[SEAL]

Attest:

DONALD J. QUIGG

Attesting Officer　　　　　Commissioner of Patents and Trademarks—Designate